United States Patent [19]
Cheruvallath et al.

[11] Patent Number: 6,040,438
[45] Date of Patent: *Mar. 21, 2000

[54] REAGENT USEFUL FOR SYNTHESIZING SULFURIZED OLIGONUCLEOTIDE ANALOGS

[75] Inventors: Zacharia S. Cheruvallath, San Diego; Vasulinga T. Ravikumar, Carlsbad; Douglas L. Cole; Daniel C. Capaldi, both of San Diego, all of Calif.

[73] Assignee: ISIS Pharmaceuticals, Inc., Carlsbad, Calif.

[*] Notice: This patent is subject to a terminal disclaimer.

[21] Appl. No.: 09/104,330

[22] Filed: Jun. 25, 1998

Related U.S. Application Data

[63] Continuation of application No. 08/811,233, Mar. 3, 1997, Pat. No. 5,902,881.

[51] Int. Cl.$^7$ .................................................. C07H 21/00
[52] U.S. Cl. .................. 536/25.3; 536/25.33; 536/25.34; 568/22
[58] Field of Search .............................. 536/25.3, 25.33, 536/25.34; 568/22

[56] References Cited

U.S. PATENT DOCUMENTS

| | | | |
|---|---|---|---|
| Re. 34,069 | 9/1992 | Köster et al. | 536/25.34 |
| 3,923,763 | 12/1975 | Edmondson | 526/217 |
| 4,310,662 | 1/1982 | Crea | 536/25.31 |
| 4,373,071 | 2/1983 | Itakura | 525/375 |
| 4,401,796 | 8/1983 | Itakura | 525/340 |
| 4,415,732 | 11/1983 | Caruthers et al. | 536/26.5 |
| 4,419,509 | 12/1983 | Hsiung | 536/25.31 |
| 4,458,066 | 7/1984 | Caruthers et al. | 536/25.34 |
| 4,500,707 | 2/1985 | Caruthers et al. | 536/25.34 |
| 4,522,735 | 6/1985 | Chasar | 508/243 |
| 4,668,777 | 5/1987 | Caruthers et al. | 536/26.5 |
| 4,689,405 | 8/1987 | Frank et al. | 536/25.3 |
| 4,725,677 | 2/1988 | Köster et al. | 536/25.34 |
| 4,816,571 | 3/1989 | Andrus et al. | 536/25.3 |
| 4,965,349 | 10/1990 | Woo et al. | 536/25.3 |
| 4,973,679 | 11/1990 | Caruthers et al. | 536/26.71 |
| 5,003,097 | 3/1991 | Beaucage et al. | 558/129 |
| 5,071,974 | 12/1991 | Groody | 536/25.34 |
| 5,132,418 | 7/1992 | Caruthers et al. | 536/25.3 |
| 5,151,510 | 9/1992 | Stec et al. | 536/25.3 |
| 5,166,387 | 11/1992 | Hirschbein | 558/129 |
| 5,218,088 | 6/1993 | Gorenstein et al. | 536/25.34 |
| 5,218,103 | 6/1993 | Caruthers et al. | 536/25.33 |
| 5,252,723 | 10/1993 | Bhatt | 536/25.3 |
| 5,252,760 | 10/1993 | Urdea et al. | 552/105 |
| 5,264,566 | 11/1993 | Froehler et al. | 536/25.34 |
| 5,292,875 | 3/1994 | Stec et al. | 536/25.33 |
| 5,310,894 | 5/1994 | Zeiger | 536/25.3 |
| 5,359,051 | 10/1994 | Cook et al. | 536/26.7 |
| 5,359,052 | 10/1994 | Stec et al. | 536/26.7 |
| 5,401,837 | 3/1995 | Nelson | 536/25.32 |
| 5,436,327 | 7/1995 | Southern et al. | 536/25.34 |
| 5,449,769 | 9/1995 | Bhatt | 536/25.3 |
| 5,510,239 | 4/1996 | Baracchini, Jr. et al. | 435/6 |
| 5,510,476 | 4/1996 | Ravikumar et al. | 536/25.31 |
| 5,512,438 | 4/1996 | Ecker | 435/6 |
| 5,512,668 | 4/1996 | Stec et al. | 536/25.33 |
| 5,514,788 | 5/1996 | Bennett et al. | 536/23.1 |
| 5,514,789 | 5/1996 | Kempe | 536/25.4 |
| 5,523,389 | 6/1996 | Ecker et al. | 536/23.1 |
| 5,571,902 | 11/1996 | Ravikumar et al. | 536/22.1 |
| 5,614,621 | 3/1997 | Ravikumar et al. | 536/25.34 |
| 5,760,209 | 6/1998 | Cheruvallath et al. | 536/25.34 |
| 5,902,881 | 5/1999 | Cheruvallath et al. | 536/25.3 |

FOREIGN PATENT DOCUMENTS

| | | |
|---|---|---|
| 8902521 | 5/1991 | Netherlands . |
| 9116331 | 10/1991 | WIPO . |
| WO 94/15946 | 7/1994 | WIPO . |
| WO 95/04065 | 2/1995 | WIPO . |
| WO 95/32980 | 12/1995 | WIPO . |
| 9609406 | 3/1996 | WIPO . |
| WO 97/19092 | 5/1997 | WIPO . |

OTHER PUBLICATIONS

Zhang et al.(I), "Synthesis and Properties of Novel Thiono Triester Modified Antisense Oligodeoxynucleotide Phosphorothioates," *Bioorganic & Medicinal Chem. Letters*, 5(15), 1735–1740 (Aug. 3, 1995).

Zhang et al. (II), "Thiono Triester Modified Antisense Oligonucleotides for Inhibition of Human Cytomegalovirus In Vitro," *Bioorganic & Medicinal Chem. Letters*, 6(16), 1911–1916 (Aug. 20, 1996).

Bokarev et al., "Synthesis of Bis(Alkyl Xanthyl) Trisulfides," *Izv. Akad. Nauk SSSR, Ser. Khim.*, 1964(12), 2175–2182; *Chem. Abstr.*, 62(7), Abstr. No. 7631d (Mar. 29, 1965); only Abstract supplied.

Scholl et al., "Novel Symmetrical and Mixed Carbamoyl and Amino Polysulfanes by Reactions of (Alkoxydichloromethyl)polysulfuranyl Substrates with N–Methylaniline," *J. Organic Chem.*, 51(10), 1866–1881 (1986).

Barany et al., "A General Strategy for Elaboration of the Dithiocarbonyl Functionality, –(C=O)SS–: Application to the Synthesis of Bis(chlorocarbonyl)disulfane and Related Derivatives of Thiocarbonic Acids," *J. Organic Chem.*, 48(24), 4750–4761 (Dec. 2, 1983).

(List continued on next page.)

Primary Examiner—L. Eric Crane
Attorney, Agent, or Firm—Oblon, Spivak, McClelland, Maier & Neustadt, P.C.

[57] ABSTRACT

The present invention is directed to a method of synthesizing sulfurized oligonucleotide analogs by reacting an oligonucleotide analog containing a phosphorous(III) linkage with a dithiocarbonic acid diester polysulfide having the formula

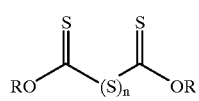

to produce a sulfurized oligonucleotide analog. The diester polysulfide reagent is useful in solution and solid phase oligonucleotide analog synthesis.

18 Claims, No Drawings

OTHER PUBLICATIONS

Carey et al., *Advanced Organic Chemistry, 3rd Ed., Part A: Structure and Mechanisms*, Plenum Press, New York, NY, 1990, only pp. 473–475 supplied.

H.C.P.F. Roelen et al., "A Study on the Use of Phenylacetyl Disulfide in the Solid–Phase Synthesis of Oligodeoxynucleoside Phosphorothioates", Recl. Trav. Chim. Pays–Bas, vol. 110, pp. 325–331, (1991). (Jul./A/.

Mitsuo Kodomari et al., "A Convenient Synthesis of Bis(Acyl) Disulfides Using Phase–Transfer Catalysis", Synthesis, Aug. (1981), pp. 637–638.

P.C.J. Kamer et al., "An Efficient Approach Toward the Synthesis of Phosphorothioate Diesters via the Schönberg Reaction", Tetrahedron Letters, vol. 30, No. 48, pp. 6757–6760, (1989).

Radhakrishnan P. Iyer et al., "A Novel Nucleoside Phosphoramidite Synthon Derived from 1R,2S–Ephedrine", Tetrahedron: Asymmetry, vol. 6, No. 5, pp. 1051–1054, (1995).

Kazunobu Miura et al., "Blockwise Mechanical Synthesis of Oligonucleotides by the Phosphoramidite Method", Chem. Pharm. Bull, vol. 35, No. 2, pp. 833–836, (1987).

Willi Bannwarth, "Synthesis of Oligodeoxynucleotides by the Phosphite–Triester Method Using Dimer Units and Different Phosphorous–Protecting Groups", Helvetica Chimica Acta, vol. 68, pp. 1907–1913, (1985).(Jul.).

G. Kumar et al., "Improvements in Oligodeoxyribonucleotide Synthesis: Methyl N,N–Dialkylphosphoramidite Dimer Units for Solid Support Phosphite", J. Org. Chem., vol. 49, pp. 4905–4912, (1984).

Radhakrishnan P. Iyer et al., "Nucleoside Oxazaphospholidines as Novel Synthons in Oligonucleotide Synthesis", J. Org. Chem., vol. 60, No. 17, pp. 5388–5389, (1995).

REAGENT USEFUL FOR SYNTHESIZING SULFURIZED OLIGONUCLEOTIDE ANALOGS

This application is a Continuation of application Ser. No. 08/811,233, filed on Mar. 3, 1997 now U.S. Pat. No. 5,902,881.

BACKGROUND OF THE INVENTION

1. Field of the Invention

The present invention is directed to a method of synthesizing sulfurized oligonucleotide analogs by reacting an oligonucleotide analog containing a trivalent phosphorous linkage with a dithiocarbonic acid diester polysulfide.

2. Discussion of the Background

It is well-known that most of the bodily states in mammals, including most disease states, are effected by proteins. By acting directly or through their enzymatic functions, proteins contribute in major proportion to many diseases in animals and man.

Classical therapeutics has generally focused on interactions with such proteins in an effort to moderate their disease causing or disease potentiating functions. Recently, however, attempts have been made to directly inhibit the production of proteins involved in disease by interacting with the messenger RNA (mRNA) molecules that direct their synthesis. These interactions have involved the hybridization of complementary, or antisense, oligonucleotides or oligonucleotides analogs to mRNA. Hybridization is the sequence-specific hydrogen bonding of an oligonucleotide or oligonucleotide analog to an mRNA sequence via Watson-Crick hydrogen bond formation. Interfering with the production of proteins involved in disease would provide maximum therapeutic results with minimum side effects.

The pharmacological activity of antisense oligonucleotides and oligonucleotide analogs depends on a number of factors that influence the effective concentration of these agents at specific intracellular targets. One important factor for oligonucleotides and analogs thereof is their stability to nucleases. It is unlikely that unmodified oligonucleotides containing phosphodiester linkages will be useful therapeutic agents because they are rapidly degraded by nucleases. Modified oligonucleotides which are nuclease resistant are therefore greatly desired.

Phosphorothioate and phosphorodithioate oligonucleotide analogs which have one or both of the non-bridging oxygens of the natural phosphodiester linkage replaced with sulphur, respectively, are especially promising antisense therapeutics. These oligonucleotide analogs are highly resistant to nucleases, have the same charge as natural phosphodiester-containing oligonucleotides, and are taken up by cells in therapeutically effective amounts. See, for example, Baracchini et al, U.S. Pat. No. 5,510,239; Ecker, U.S. Pat. No. 5,512,438; Bennett et al, U.S. Pat. No. 5,514,788; and Ecker et al, U.S. Pat. No. 5,523,389.

Phosphorothioate and phosphorodithioate oligonucleotide analogs are conveniently synthesized with automated DNA synthesizers using hydrogen phosphonate chemistry which permits the phosphonate backbone to be sulfurized in a single step after automated synthesis. One drawback of this approach is that coupling yields during chain synthesis are typically lower than those obtained using phosphoramidite chemistry. The final yield of the desired oligonucleotide analog is therefore too low due to the low individual coupling yields.

Automated synthesis using phosphoramidite chemistry is a highly desirable approach to the synthesis of these sulfurized oligonucleotide analogs, with coupling yields typically greater than 99%. However, the phosphorous(III)-containing phosphite intermediates are unstable under the conditions of the detritylation step of the synthesis cycle. Therefore, these phosphorous(III) linkages must be sulfurized after each coupling step.

A more recent method for the synthesis of oligonucleotide analogs is the "blockmer" approach. In blockmer synthesis, an oligonucleotide analog is made by the sequential coupling of short protected oligomers or blocks, e.g., a dinucleotide, on a solid support. This strategy offers several advantages over the conventional synthetic approach which involves the sequential coupling of monomeric nucleoside phosphoramidites. The number of synthesis cycles required to prepare an oligonucleotide analog is reduced, saving time and minimizing reagent consumption. The blocks may be prepared on a large scale using inexpensive solution phase synthesis techniques. In order to prepare sulfurized oligonucleotide analogs by the blockmer method, a reagent for sulfuring the phosphorous(III) linkages of the blocks on a large scale is required. The blockmer approach is described in the following references: Ravikumar et al, WO 95/32980; WO 94/15947; *Journal of Organic Chemistry* 1984, 49, 4905–4912; *Helevetica Chimica Acta* 1985, 68, 1907–1913; *Chem. Pharm. Bull.* 1987, 35, 833–836.

There are several reagents available for sulfurizing the phosphite intermediates during automated oligonucleotide synthesis. All of these reagents have drawbacks which limit their use for synthesizing sulfurized oligonucleotide analogs.

Elemental sulfur, for example, has been used to sulfurize phosphorous(III) linkages in solid phase oligonucleotide synthesis. However, elemental sulphur is not suitable for use with automated synthesizers because of its poor solubility in standard solvents and slow sulfurization rate. In addition, carbon disulfide, the preferred solvent for elemental sulphur, is highly volatile and has a low flash point. See, U.S. Pat. Nos. 5,252,723 and 5,449,769.

The Beaucage reagent, 3H-1,2-benzodithiol-3-one, is a considerably more efficient sulfurizing agent. However, this reagent precipitates from solution and clogs the solvent and reagent transfer lines of an automated DNA synthesizer. Also, the by-product formed during the sulfurization reaction is a potent oxidizing agent. This by-product can lead to side products, e.g., phosphodiesters, which are difficult to separate from the desired sulfurized oligonucleotides. In addition, the preparation of this reagent involves expensive and toxic materials, and is therefore not amenable for large-scale synthesis of sulfurized oligonucleotide analogs. See, U.S. Pat. No. 5,003,097.

Tetraethylthiuram disulfide is an inexpensive and chemically stable sulfurization reagent. However, the sulfurization rate is slow and therefore a significant molar excess of this reagent is required. Even with an excess of this reagent, sulfurization yields are unacceptably low. See, U.S. Pat. No. 5,166,387.

Phenylacetyl disulfide may be used to sulfurize phosphite intermediates during automated oligonucleotide synthesis. However, this reagent has not been reported to be useful for large-scale synthesis of sulfurized oligonucleotide analogs. See, *Recherches Travaux Chimiques des Pays-Bas* 1991, 110, 325–331; *Tetrahedron Letters* 1989, 30, 6757–6760; *Synthesis* 1981, 637–638.

Accordingly, there remains a need in the art for methods and reagents for synthesizing sulfurized oligonucleotide analogs which overcome these problems.

SUMMARY OF THE INVENTION

An object of the present invention is to provide a method of synthesizing a sulfurized oligonucleotide using a reagent that efficiently sulfurizes a phosphorous(III) linkage in an oligonucleotide analog.

Another object of the present invention is to provide a method of synthesizing a sulfurized oligonucleotide using a reagent that does not require the use of solvents having a high volatility and flash point.

Another object of the present invention is to provide a method of synthesizing a sulfurized oligonucleotide using a reagent that is highly soluble in organic solvents and does not precipitate from solution.

Another object of the present invention is to provide a method of synthesizing a sulfurized oligonucleotide using a reagent that is useful in automated solid phase synthesis of oligonucleotide analogs.

Another object of the present invention is to provide a method of synthesizing a sulfurized oligonucleotide using a reagent that is compatible with large-scale and small-scale synthesis using solution phase methods.

Another object of the present invention is to provide a sulfurizing reagent composition that may be used to sulfurize a phosphorous(III) linkage of an oligonucleotide analog.

These objects and others may be accomplished with a method of synthesizing a sulfurized oligonucleotide analog by reacting an oligonucleotide analog containing a phosphorus(III) linkage capable of being sulfurized with a thiodicarbonic acid diester polysulfide having the formula:

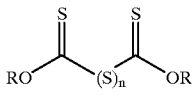

where each R is an inert side chain, and n is 2, 3 or 4.

The above objects may also be accomplished with a method of synthesizing a sulfurized oligonucleotide analog by:
(a) providing a nucleoside analog having a blocked hydroxyl group;
(b) deblocking the blocked hydroxyl group to produce a free hydroxyl group;
(c) reacting the free hydroxyl group with a protected nucleoside analog phosphoramidite or a protected nucleoside analog phosphorothioamidite having a blocked hydroxyl group to produce an oligonucleotide analog containing a phosphorous(III) linkage and a blocked hydroxyl group;
(d) reacting the phosphorous(III) linkage with a reagent selected from the group consisting of an oxidizing agent and a dithiocarbonic acid diester polysulfide to produce an oxidized or sulfurized phosphorous(V) linkage;
(e) repeating steps (b) through (d) at least once to produce a sulfurized oligonucleotide analog, wherein at least one step (d) in the method is reacting the phosphorous (III) linkage with the dithiocarbonic acid diester polysulfide of the present invention.

The above objects may also be accomplished with a sulfurizing reagent composition containing an effective amount of thiodicarbonic acid diester polysulfide for sulfurizing a phosphorous(III) linkage of an oligonucleotide analog and at least one solvent.

DETAILED DESCRIPTION OF THE INVENTION

A more complete appreciation of the invention and many of the attendant advantages thereof will be readily obtained as the same becomes better understood by reference to the following detailed description.

As used in the present invention, the term "oligonucleotide analog" includes linear oligomers of natural or modified nucleosides linked by phosphodiester bonds or analogs thereof ranging in size from two monomeric units to several hundred monomeric units. Oligonucleotide analogs include modifications of the heterocyclic base moiety and/or the sugar portion of a component nucleotide. In particular, the term includes non-natural oligomers containing phosphorus (III) linkages which are amenable to sulfurization. Preferably, the modifications do not inhibit the ability of an oligonucelotide analog to bind to a target nucleic acid. The term "sulfurized oligonucleotide analog" is an oligonucleotide analog containing at least one analog of a phosphodiester linkage in which one or both of the non-bridging oxygen atoms are replaced by sulfur. The term "nucleoside analog" refers to a natural or modified nucleoside. In particular, this term includes nucleosides that are modified at the heterocyclic base and/or sugar to enhance hybridization to the target nucleic acids. It is to be understood that the stereochemical relationship between the sugar substituents in the nucleoside and oligonucleotide analogs disclosed herein is preferably the same as that of naturally-occurring DNA and RNA, see G. M. Blackburn and M. J. Gait (eds.), *Nucleic Acids in Chemistry and Biology* (ILR Press, 1990), Chapter 2, pp. 19–70.

The thiodicarbonic acid diester polysulfide of the present invention preferably has the formula:

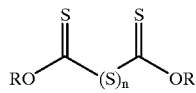

where each R is preferably an inert group. These groups preferably do not contain any reactive moieties which could lead to side reactions or poor yields in the sulfurization reaction. Preferably, each R is independently $C_1-C_8$ alkyl, substituted $C_1-C_8$ alkyl, $C_2-C_8$ heterocycloalkyl containing up to three heteroatoms, substituted $C_2-C_8$ heterocycloalkyl containing up to three heteroatoms, $C_6-C_{14}$ aryl, substituted $C_6-C_{14}$ aryl, $C_3-C_{11}$ hetaryl containing up to three heteroatoms, substituted $C_3-C_{11}$ hetaryl containing up to three heteroatoms, $C_7-C_{18}$ aralkyl, substituted $C_7-C_{18}$ aralkyl, $C_4-C_{15}$ heterocycloaralkyl containing up to three heteroatoms or substituted $C_4-C_{15}$ heterocycloaralkyl containing up to three heteroatoms. The term "$C_1-C_8$ alkyl" includes linear, branched and cyclic alkyl groups. The term "substituted" means that up to three hydrogen atoms in the group are substituted with up to three halogen, nitro, cyano, $C_1-C_8$ alkyl, O—$C_1-C_8$ alkyl, N—$C_1-C_8$ alkyl, S—$C_1-C_8$ alkyl groups or combinations thereof. More preferably, each R is independently $C_2-C_8$ alkyl, $C_6-C_{14}$ aryl or substituted $C_6-C_{14}$ aryl. Most preferably, each R is independently ethyl or p-chlorophenyl. The dithiocarbonic acid diester polysulfide may be a disulfide, trisulfide or tetrasulfide, i.e., n is 2, 3 or 4, respectively. Preferably n is 2 or 3, and more preferably, n is 2.

The thiodicarbonic acid diester polysulfide may be prepared by oxidation of the corresponding thiodicarbonic acid or acid salt with oxidizing agents, such as iodine or bromine. Methods of synthesis and properties of these polysulfides are described in the following references: Barany et al, *Journal of Organic Chemistry*, 1983, 48, 4750–4761; W. F. Zeise, *J. Prakt. Chem.* 1845, 36, 352–362; Losse et al., *J. Prakt. Chem.* 1961, 13, 260; S. R. Rao, *Xanthates and Related*

*Compounds,* (M. Decker, New York, 1971); Bulmer et al, *J. Chem. Soc.* 1945, 674–677.

The thiodicarbonic acid diester polysulfide of the present invention is an efficient reagent for sulfurizing phosphorous (III) linkages in oligonucleotide analogs. The reagent does not precipitate out of solution, even on prolonged storage. The reagent may be used in solution phase synthesis and is particularly useful in solid-phase synthesis of oligonucleotide analogs with automated DNA synthesizers. The reagent is particularly useful in large-scale synthesis, using either solution phase or solid phase techniques.

When used to sulfurize phosphorus(III) linkages in oligonucleotide analogs, the thiodicarbonic acid diester polysulfide is preferably delivered to the oligonucleotide analog in a suitable organic solvent, such as acetonitrile, pyridine, tetrahydrofuran, dichloromethane, dichloroethane and collidine. These solvents may be used singly or as mixtures in any proportion. Preferable solvents are pyridine, dichloromethane and mixtures thereof. Pyridine is most preferred. The reagent may be used at any effective concentration for sulfurizing a phosphorous(III) linkage, preferably between 0.01 M to 1.5 M, more preferably from 0.2 to 1.2 M; and most preferably from 0.5 to 1.0 M.

The sulfurization reaction may be conducted at any convenient temperature, preferably from 0 to 70° C.; more preferably from 10 to 40° C.; and most preferably at about room temperature, i.e., 18 to 25° C. The sulfurization reaction is preferably conducted for 30 seconds to 15 minutes, more preferably, 1 to 15 minutes; and most preferably, 3 to 10 minutes. Preferably, sulfurization is performed under anhydrous conditions with the exclusion of air.

The present method for synthesizing a sulfurized oligonucleotide analog may be applied to any oligonucleotide analog containing at least one phosphorus(III) linkage which is amenable to sulfurization. In particular, the present method is useful for sulphurizing phosphite triesters, thiophosphite triesters, and hydrogen phosphonates. More preferably, the phosphorus(III) linkage is a phosphite triester or a thiophosphite triester. Most preferably, the phosphorus (III) linkage is a phosphite triester.

Detailed procedures for synthesizing oligonucleotide analogs containing at least one phosphorus(III) linkages are well-known in the art and are described in the following references: M. J. Gait (ed.), *Oligonucleotide Synthesis, A Practical Approach* (ILR Press, 1984); J. S. Cohen (ed.), *Oligonucleotides: Antisense Inhibitors of Gene Expression,* (CRC Press, Inc., Boca Raton, Fla., 1989).

Preferably, the dithiocarbonic acid diester polysulfide of the present invention is used in conjunction with the phosphoramidite or phosphorothioamidite synthetic approaches. Synthesis may be conducted in solution phase or using solid phase techniques. More preferably, the synthesis is conducted using a solid support. Most preferably, the synthesis is conducted on a solid support using an automated DNA synthesizer, e.g., an APPLIED BIOSYSTEMS model 380B or a similar machine.

Preferably, this synthetic approach involves the following steps: (1) deprotecting a blocked reactive functionality on the growing oligonucleotide analog chain or on the first nucleoside analog monomer, to produce a deblocked reactive functionality, (2) reacting an appropriately blocked and protected nucleoside analog phosphoramidite or phosphorothioamidite monomer with the deblocked reactive functionality of the growing nucleotide analog chain, preferably in the presence of an activator, to form an oligonucleotide analog containing a phosphorus(III) linkage, (3) capping any unreacted functionalities, and (4) sulfurizing the newly-formed phosphorus(III) linkage with the thiodicarbonic acid diester polysulfide to obtain the phosphorus atom in a sulfurized pentacoordinate state.

The term "blocked" means that a reactive functionality, usually a nucleophile, e.g., a 5' hydroxyl, is protected with a group that may be selectively removed. Preferably, these blocking groups are labile to dilute acid, e.g. dichloroacetic acid in dichloromethane, and are stable to base. Preferable blocking groups include 4,4'-dimethoxytrityl (DmTr), monomethoxytrityl, diphenylmethyl, phenylxanthen-9-yl (pixyl) or 9-(p-methoxyphenyl)xanthen-9-yl (Mox). The 4,4'-dimethoxytrityl group is most preferred. Throughout the present disclosure the labile 5' blocking group is represented as "$R^6$".

Any natural or non-natural heterocyclic base may be used in the present invention, such as adenine, guanine, cytosine, thymine, uracil, 2-aminopurine, inosine, substituted pyrimidines, e.g., 5-methylcytosine, and 5-nitropyrrole. Other suitable heterocyclic bases are described by Merigan et al., U.S. Pat. No. 3,687,808. Preferably, the heterocyclic base is attached to C-1 of the sugar moiety of nucleoside analog phosphoramidite (1) via a nitrogen of the base. Throughout the present disclosure the heterocyclic base is respresented as "B".

During synthesis these heterocyclic groups are preferably protected to prevent any reactive group, e.g., an exocyclic amino group, to prevent undesired side reactions. The term "protected" means that reactive moieties such as exocyclic amino groups, 2'-hydroxyl groups, oxygen or sulfur bonded to phosphorus atoms, and the like, have protective groups which are generally removed after synthesis of the oligonucleotide analog is completed. Preferably, these protective groups are labile to a base and/or a nucleophile. This term also includes oligonucleotide and nucleoside analogs which have groups that do not require such protection, e.g., heterocyclic bases such as thymine or abasic nucleosides.

Preferable protecting groups for the heterocyclic bases include base labile groups. The exocyclic amino groups of the heterocyclic groups are preferably protected with acyl groups that are removed by base treatment after synthesis of the sulfurized oligonucleotide analog. Preferably, these protecting groups are $C_2$–$C_{10}$ acyl groups. N-benzoyl and N-isobutyryl protecting groups are particularly preferred. Adenine is preferably protected as an $N^2$-isobutyryl derivative. Guanine is preferably protected as an $N^6$-isobutyryl derivative. Cytidine is preferably protected as an $N^4$-benzoyl derivative.

The sulfurized nucleotide analogs of the present invention may be substituted at the 2' position. Preferable 2' substituents are groups that enhance the hybridization of an oligonucleotide analog with its target nucleic acid, a group that improves the in vivo stability of an oligonucleotide analog or enhances the pharmacokinetic and/or pharamacodynamic properties of an oligonucleotide analog. Examples of 2' substituents include hydrogen, hydroxyl, F, Cl, Br, $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms, substituted $C_4$–$C_{15}$ heterocycloaralkyl containing up to three heteroatoms, O—$C_1$–$C_8$ alkyl, substituted O—$C_1$–$C_8$ alkyl (such as $CF_3$), O—$C_2$–$C_8$ heterocycloalkyl containing up to three heteroatoms, substituted O—$C_2$–$C_8$ heterocycloalkyl containing up to three heteroatoms, O—$C_6$–$C_{14}$ aryl (such as phenyl), substituted O—$C_6$–$C_{14}$ aryl, O—$C_3$–$C_{11}$ hetaryl containing up to three heteroatoms, substituted O—$C_3$–$C_{11}$ hetaryl containing up to three heteroatoms, O—$C_7$–$C_{18}$ aralkyl (such as benzyl), substituted O—$C_7$–$C_{18}$ aralkyl, O—$C_4$–$C_{15}$ heterocycloaralkyl containing up to three heteroatoms, substituted O—$C_4$–$C_{15}$ heterocycloaralkyl containing up to three heteroatoms, O—$C_1$–$C_8$-alkyl-O—$C_1$–$C_8$-alkyl, O—$C_1$–$C_8$ alkenyl, O—$C_1$–$C_8$ alkoxyamino, O-tri-$C_1$–$C_8$-alkyl silyl (such as tert-butyldimethylsilyl) substituted O-tri-$C_1$–$C_8$-alkyl silyl, NH—$C_1$–$C_8$ alkyl, N—($C_1$–$C_8$)$_2$, NH—$C_1$–$C_8$ alkenyl, N—($C_1$–$C_8$)$_2$ alkenyl, S—$C_1$–$C_8$ alkyl, S—$C_1$–$C_8$ alkenyl, $NH_2$, $N_3$, NH—$C_1$–$C_8$-alkyl-$NH_2$, polyalkylamino and an RNA cleaving group. Preferable RNA cleaving groups include the O-{3-propoxy-[2-naphthyl-7-(1-(dimethylaminosulfonyl)-imidazol-4-yl)]} group and the O-{3-propoxy-[2-naphthyl-7-(1-(dimethylaminosulfonyl-2-methoxy-5-acetylaminomethyl)-imidazol- 4-yl)]} group. These groups are discussed by Cook et al, U.S. Pat. No. 5,359,051.

Preferably, the 2' substituents are hydrogen, hydroxyl, O—$C_1$–$C_8$ alkyl, F, O—$C_1$–$C_8$-alkoxyamino and O—$C_1$–$C_8$-alkyl-O—$C_1$–$C_8$-alkyl. More preferably, the 2' substituents are hydrogen, O—$C_1$–$C_8$ alkyl, F and O—$C_1$–$C_8$-alkyl-O—$C_1$–$C_8$-alkyl. Most preferably, the 2' substituent is hydrogen or a methoxyethoxy group. Throughout the present disclose, the 2' substituent is respresented as "X".

A variety of protecting groups for the oxygen and sulfur atoms attached to the phosphorus atom in the nucleoside analog phosphoramidite and phosphorothioamidite, respectively, may be used. These protecting groups are preferably removed at after synthesis is complete. Preferably, these protecting groups are labile to a base and/or a nucleophile. Most prefereably, these protecting groups are removed by aqueous ammonium hydroxide. Preferable protecting groups are 2-cyanoethyl, 4-cyano-2-butenyl, 2-diphenylmethylsilylethyl (DPSE) or a 2-N-amidoethyl group having the formula $R^1CONR^2CHR^3CHR^4$—. These protecting groups are preferably removed after synthesis, preferably with an aqueous solution of ammonia at a temperature between room temperature and 75° C. In the present invention, the terms "phosphodiester linkage", "phosphorothioate linkage" and "phosphorodithioate linkage" describe these internucleosidic linkages in protected or unprotected form. Throughout the present disclosure, these phosphorous protecting groups will be represented as "Pg". An oxygen atom or sulfur atom attached to the phosphorous atom in a nucleoside analog phosphoramidite or thiophosphoramidite or an oligonucleotide analog is represenated as "Y". Preferably, Y is an oxygen atom.

The 4-cyano-2-butenyl protecting group is removed by δ-elimination, preferably using the standard $NH_3/H_2O$ deprotection conditions known in the art. 4-cyano-2-butenyl-protected nucleoside analog phosphoramidites may be prepared with 4-cyano-2-butene-1-ol and appropriately protected nucleoside analogs using known synthetic methodology. The synthesis of 4-cyano-2-butene-1-ol is disclosed by Ravikumar et al, *Synthetic Communications* 1996, 26(9), 1815–1819.

The 2-diphenylmethylsilylethyl (DPSE) protecting group is described in Ravikumar et al., WO 95/04065. This protecting group may be removed by treatment with a base, preferably aqueous ammonium hydroxide. The DPSE group may also be removed with fluoride ion. Preferably, the fluoride ion is provided from a salt such as a tetraalkylammonium fluoride, e.g., tetrabutylammonium fluoride (TBAF) or an inorganic fluoride salt, e.g., potassium fluoride or cesium fluoride in a solvent such as tetrahydrofuran, acetonitrile, dimethoxyethane or water.

The 2-N-amidoethyl group is described in the commonly assigned application U.S. patent application Ser. No. 7761-0002-55, U.S. Pat. No. 5,760,209 (Title: Protecting Group for Synthesizing oligonucleotide Analogs, Attorney Docket No. 7761-002-55). The 2-N-amidoethyl group has the formula $R^1CONR^2CHR^3CHR^4$-, where $R^1$ is $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms or substituted $C_4$–$C_{15}$ heterocycloaralkyl containing up to three heteroatoms. More preferably, $R^1$ is $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms or substituted $C_3$–$C_{11}$ hetaryl containing up to three heteroatoms. Even more preferably, $R^1$ is methyl, fluoromethyl, difluoromethyl or trifluoromethyl. Most preferably, $R^1$ is methyl, trifluoromethyl or phenyl.

The nitrogen atom of the 2-N-amidoethyl group may be unsubstituted, i.e., $R^2$ may be hydrogen, or substituted. Preferably, $R^2$ is hydrogen, $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms or substituted $C_4$–$C_{15}$ heterocycloaralkyl containing up to three heteroatoms. More preferably, $R^2$ is hydrogen or $C_1$–$C_8$ alkyl. Most preferably, $R^2$ is hydrogen or methyl.

The ethyl moiety of the 2-N-amidoethyl group may be unsubstituted, e.g., $R^3$ and $R^4$ may both be hydrogen. Alternatively, the ethyl moiety may be substituted with groups that preferably do not compromise the stability of the 2-N-amidoethyl group during oligonucleotide analog synthesis and permit the protecting group to be removed by treatment with a base and/or a nucleophile following stepwise assembly of an oligonucleotide analog. Preferable $R^3$ and $R^4$ groups are hydrogen, $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms or substituted $C_4$–$C_{15}$ heterocycloaralkyl containing up to three heteroatoms. More preferably, $R^3$ is hydrogen or linear $C_1$–$C_8$ alkyl. Most preferably, $R^3$ is hydrogen or methyl. More preferably, $R^4$ is hydrogen, $C_6$–$C_{14}$ aryl, substituted $C_6$–$C_{14}$ aryl, $C_3$–$C_{11}$ hetaryl containing up to three heteroatoms or substituted $C_3$–$C_{11}$ hetaryl containing up to three heteroatoms. Most preferably, $R^4$ is hydrogen or phenyl. The $R^3$ and $R^4$ groups are independently selected, i.e., they may be the same or different.

Alternatively, $R^3$ and $R^4_1$ together with the carbon atoms they are bonded to, may form a $C_3$–$C_8$ cycloalkyl group, a substituted $C_3$–$C_8$ cycloalkyl group, a $C_2$–$C_8$ heterocycloalkyl group containing up to three heteroatoms or a substituted $C_2$–$C_8$ heterocycloalkyl group containing up to three heteroatoms. In this embodiment, $R^3$ and $R^4$, together with the carbon atoms they are bonded to, preferably form a $C_3$–$C_8$ cycloalkyl group or a substituted $C_3$–$C_8$ cycloalkyl group. More preferred cycloalkyl groups are $C_4$–$C_7$ or substituted $C_4$–$C_7$ groups, with $C_5$–$C_6$ or substituted $C_5$–$C_6$ groups most preferred. An unsubstituted cycloalkyl group is particularly preferred. An unsubstituted $C_6$ cycloalkyl group is most particularly preferred. The stereochemical relationship between the N-amido group and Y may be cis or trans. A trans relationship is preferred.

An allyl group is also a preferable protecting group for the oxygen or sulfur atom attached to the phosphorus atom in an oligonucleotide analog. The allyl protecting group is described in U.S. Pat. No. 5,026,838. The term "allyl group" includes allyl, methallyl, crotyl, prenyl, geranyl, cinnamyl and p-chlorocinnamyl groups. The number of carbon atoms in these groups is preferably 3 to 10. Preferably, the allyl group is an unsubstituted allyl group. The allyl group may be removed with a palladium(0) compound and a nucleophilic agent, such as an amine or a formic acid salt, under neutral conditions at room temperature. A preferred reagent is tetrakis(triphenylphosphine) palladium(0) and n-butylamine in tetrahydrofuran.

An activator is generally used in the coupling of a deblocked reactive functionality on the oligonucleotide or nucleoside analog and the phosphoramidite or phosphorothioamidite monomer. Preferable activators are well-known in the art, such as 1H-tetrazole, 5-(4-nitrophenyl)-1H-tetrazole and diisopropylamino tetrazolide. 1H-Tetrazole is most preferred.

A capping step is preferably used after this coupling reaction to permanently block all uncoupled reactive functionalities. Suitable capping reagents are well-known in the art. A preferable capping reagent is acetic anhydride/lutidine/THF (1:1:8) with N-methylimidazole/THF.

When synthesis is performed by solution phase methods, the 3' terminal hydroxyl group of an oligonucleotide analog is preferably protected to prevent the 3' hydroxyl group from participating in any undesired side reactions. Preferably, the terminal 3' hydroxyl group is protected with a group which may be removed selectively without removing any other protecting groups. A $C_2$–$C_{10}$ acyl group is preferred. The acetyl or levulinyl group is more preferred. The levulinyl group is most preferred. Throughout the present disclosure this 3' protecting group is represented as "$R^7$".

The sequential addition of nucleoside analog phosphoramidites or phosphorothioamidites may be repeated until an oligonucleotide analog having the desired sequence length is obtained. The length of the sulfurized oligonucleotide analog is preferably 2 to 200 monomer units; more preferably, 2 to 100 monomer units; even more preferably, 2 to 50 monomer units; and, most preferably, 2 to 25 monomer units. These ranges include all subranges therebetween.

In a preferred embodiment of the present invention, a sulfurized oligonucleotide analog is synthesized on a solid support. Suitable solid supports include controlled pore glass (CPG); oxalyl-controlled pore glass, see for example Alul et al, *Nucleic Acids Research* 1991, 19, 1527; *TENTA-GEL Support*, see Wright et al, *Tetrahedron Letters* 1993, 34, 3373; POROS, a polystyrene resin available from PERCEP-TIVE BIOSYSTEMS; and a polystyrene/ divinylbenzene copolymer. Controlled pore glass is the most preferred solid support. Throughout the present discloure the solid support is represented as "$S^P$".

The oligonucleotide analog is preferably attached to the solid support by a group which may be easily cleaved to release the oligonucleotide analog from the solid support when synthesis is complete. Preferably, this group may be cleaved upon exposure to a base and/or a nucleophile. More preferably, the group is an acyl. Most preferably, the group is a carboxyl group esterifed with the terminal 3' hydroxyl group of the oligonucleotide analog. The group linking an oligonucleotide analog to a solid support is represented as "L" in the present disclosure.

The present invention includes sulfurized oligonucleotide analogs containing phosphorothioate, phosphorodithioate, and phosphodiester linkages in any combination. The sulfurized oligonucleotide analogs of the present invention may contain only sulfurized linkages, e.g., phosphorothioate and/or phosphorodithioate. The oligonucleotide analogs may also contain one or more phosphodiester linkages in addition to the sulfurized linkages. In a preferred embodiment, the sulfurized oligonucleotide analog contains both phosphorothioate and phosphodiester linkages. In another preferred embodiment, the oligonucleotide contains both phosphorodithioate and phosphodiester linkages.

Phosphodiester linkages are formed by oxidizing a phosphorous(III) linkage with any suitable oxidizing reagent known in the art, e.g., $I_2$/THF/$H_2O$, $H_2O_2$/$H_2O$, tert-butyl hydroperoxide or a peracid, such as m-chloroperbenzoic acid. $I_2$/THF/$H_2O$ is a preferred oxidizing agent.

In a preferred embodiment, the oligonucleotide analog containing at least one phosphorous(III) linkage has the formula:

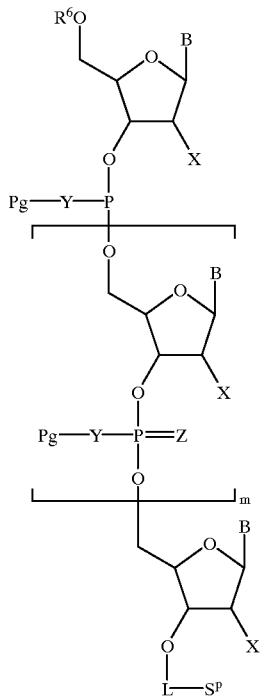

where each Pg is independently a group labile to a base and/or a nucleophile or an allyl group;

$R^6$ is a labile blocking group;

each B is independently an unprotected or protected heterocyclic base;

each X is independently selected from the group consisting of hydrogen, hydroxyl, F, Cl, Br, $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms, substituted $C_4$–$C_{15}$ heterocycloaralkyl containing up to three heteroatoms, O—$C_1$–$C_8$ alkyl, substituted O—$C_1$–$C_8$ alkyl, O—$C_2$–$C_8$ heterocycloalkyl containing up to three heteroatoms, substituted O—$C_2$–$C_8$ heterocycloalkyl containing up to three heteroatoms, O—$C_6$–$C_{14}$ aryl, substituted O—$C_6$–$C_{14}$ aryl, O—$C_3$–$C_{11}$ hetaryl containing up to three heteroatoms, substituted O—$C_3$–$C_{11}$ hetaryl containing up to three heteroatoms, O—$C_7$–$C_{18}$ aralkyl, substituted O—$C_7$–$C_{18}$ aralkyl, O—$C_4$–$C_{15}$ heterocycloaralkyl containing up to three heteroatoms, substituted O—$C_4$–$C_{15}$ heterocycloaralkyl containing up to three heteroatoms, O—$C_1$–$C_8$-alkyl-O—$C_1$–$C_8$-alkyl, O—$C_1$–$C_8$ alkenyl, O—$C_1$–$C_8$ alkoxyamino, O-tri-$C_1$–$C_8$-alkyl silyl, substituted O-tri-$C_1$–$C_8$-alkenyl, silyl, NH—$C_1$–$C_8$ alkyl, N—($C_1$–$C_8$)$_2$, NH—$C_1$–$C_8$ alkenyl, N—($C_1$–$C_8$)$_2$ alkenyl, S—$C_1$–$C_8$ alkyl, S—$C_1$–$C_8$ alkenyl, $NH_2$, $N_3$, NH—$C_1$–$C_8$-alkyl-$NH_2$, polyalkylamino and an RNA cleaving group;

each Y is independently O or S;

each Z is independently O or S;

L is a group labile to a nucleophile and/or base;

$S^p$ is a solid support; and m is 0 or a positive integer.

Preferred protecting groups, Pg, include 2-cyanoethyl, 4-cyano-2-butenyl, 2-diphenylmethylsilylethyl (DPSE) and a 2-N-amidoethyl group.

In a preferred embodiment, the oligonucleotide analog containing a phosphorous(III) linkage contains 2 to 100 monomer units, i.e., m is 0 to 98; more preferably, from 2 to 50 monomer units, i.e., m is 0 to 48; and most preferably from 2 to 25 monomer units, i.e., m is 0 to 23.

Treating the above oligonucleotide analog with a dithiocarbonic acid diester polysulfide affords the corresponding sulfurized oligonucleotide analog having the formula:

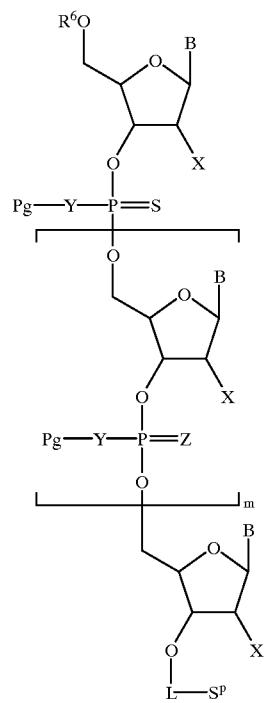

where Pg, $R^6$, B, X, Y, Z, L, S and m are defined above. Z is an oxygen atom or a sulfur atom. Appropriate choice of Z allows the internucleosidic linkage containing Z to be a phosphodiester, phosphorothioate or phosphorodithioate linkage, depending on selection of Y. For example, when Y and Z are both oxygen the linkage is a phosphodiester. When Y is oxygen and Z is sulfur, or vice versa, the linkage is a phosphorothioate. When Y and Z are both sulfur the linkage is a phosphorodithioate. Preferably, Y is an oxygen atom and Z is a sulfur atom which has been introduced using the dithiocarbonic acid diester polysulfide described above. It is to be understood that the terms phosphodiester, phosphorothioate and phosphorodithioate refer to the internucleotide linkage after removal of the Pg groups.

Following sulfurization, the sequence of the sulfurized oligonucleotide analog may be further extended. Alternatively, the sulfurized oligonucleotide analog may be deprotected and removed from the solid support to afford the corresponding deprotected sulfurized analog. The deprotected sulfurized analog may contain phosphorothioate, phosphorodithioate and phosphodiester linkages, in any combination.

In another preferred embodiment of the present invention, the oligonucleotide analog containing at least one phosphorous(III) linkage is a dinucleotide having the formula:

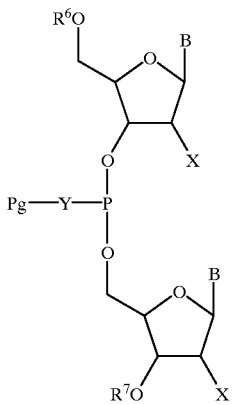

where $R^7$ is a group labile to a base and/or a nucleophile. Sulfurization of the dinucleotide analog with the dithiocarbonic acid diester polysulfide affords the corresponding sulfurized dinucleotide analog having the formula:

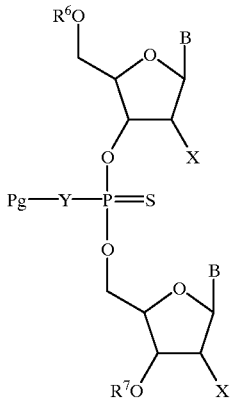

The present invention also provides a method for synthesizing a sulfurized oligonucleotide analog by:

(a) providing a nucleoside analog having a blocked hydroxyl group;

(b) deblocking the blocked hydroxyl group to obtain a free hydroxyl group;

(c) reacting the free hydroxyl group with a protected nucleoside analog phosphoramidite having a blocked hydroxyl group to produce an oligonucleotide analog containing a phosphorous(III) linkage and a blocked hydroxyl group;

(d) reacting the phosphorous(III) linkage with a reagent selected from the group consisting of an oxidizing agent and a dithiocarbonic acid diester polysulfide having the formula:

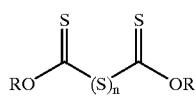

to produce an oxidized or sulfurized phosphorous(V) linkage;

(e) repeating steps (b) through (d) at least once to produce a sulfurized oligonucleotide analog; where the oligonucleotide analog contains at least one sulfurized phosphorous(V) linkage. Preferably, each phosphorous (V) linkage is sulfurized.

A preferred nucleoside analog phosphoramidite having a blocked hydroxyl group used in step (c) has the formula:

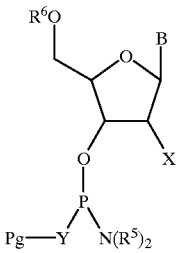

The $R^5$ groups are chosen such that the nucleoside analog phosphoramidite preferably couples efficiently with a reactive group on the on the growing oligonucleotide analog chain, e.g., a 5' hydroxyl group, to form a phosphorous(III) internucleotide linkage. The $R^5$ groups are independently selected, i.e., they may be the same or different. Preferable $R^5$ groups are $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms or substituted $C_4$–$C_{15}$ heterocycloaralkyl containing up to three heteroatoms; or both $R^5$ groups together with the nitrogen atom they are bonded to form a $C_2$–$C_8$ heterocycloalkyl group containing up to three heteroatoms, a substituted a $C_2$–$C_8$ heterocycloalkyl group containing up to three heteroatoms, a $C_3$–$C_{11}$ hetaryl group containing up to three heteroatoms or a substituted $C_3$–$C_{11}$ hetaryl group containing up to three heteroatoms. More preferably, the $R^5$ groups are each a $C_1$–$C_8$ alkyl group or together with the nitrogen atom they are bonded to form a $C_2$–$C_8$ heterocycloalkyl group containing up to three heteroatoms. Even more preferably, each $R^5$ group is a branched $C_1$–$C_8$ alkyl group. Most preferably, both $R^5$ groups are isopropyl.

In a preferred embodiment, the nucleoside analog in step (a) is attached to a solid support. A preferred nucleoside analog attached to a solid support has the formula:

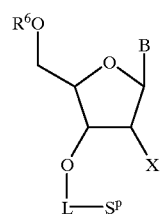

In another embodiment, the oligonucleotide analog containing a phosphorous(III) linkage and a blocked hydroxyl group is attached to a solid support and has the formula:

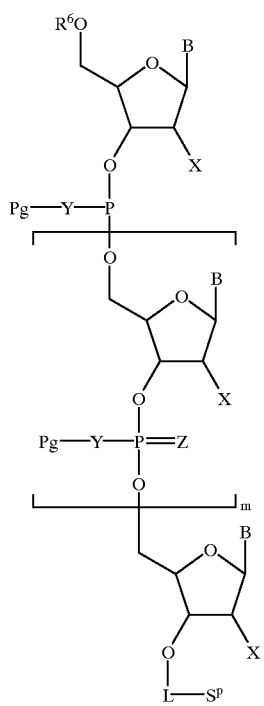

and the resulting sulfurized oligonucleotide analog has the formula:

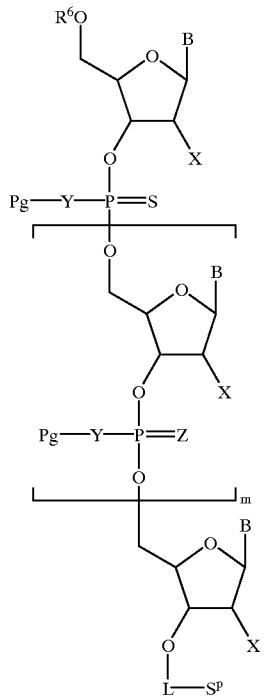

The sulfurized oligonucleotide analog synthesized on a solid support may be removed from the support, preferably by base treatment. Preferably, all of the protecting groups are removed during cleavage from the solid support. Preferable reagents for cleaving the sulfurized oligonucleotide analog from the solid support are aqueous ammonium hydroxide and ammonia/methanol solutions. The simultaneous deprotection and removal of the sulfurized oligonucleotide analog is preferably accomplished in aqueous ammonium hydroxide at a temperature between room temperature, i.e., 18 to 25° C., and 75° C.; more preferably, between room temperature and 65° C.; and most preferably, between room temperature and 60° C. A temperature of 55° C. is particularly preferred. The deprotection reaction time is preferably 1 to 30 hours; more preferably, 1 to 24 hours; and most preferably, 12–24 hours. The concentration of ammonium hydroxide in the solution used for deprotection is preferably 20 to 30% by weight; more preferably, 25 to 30% by weight; and most preferably, 28 to 30% by weight.

In a preferred embodiment, the sulfurized oligonucleotide analog released from the solid support has the formula:

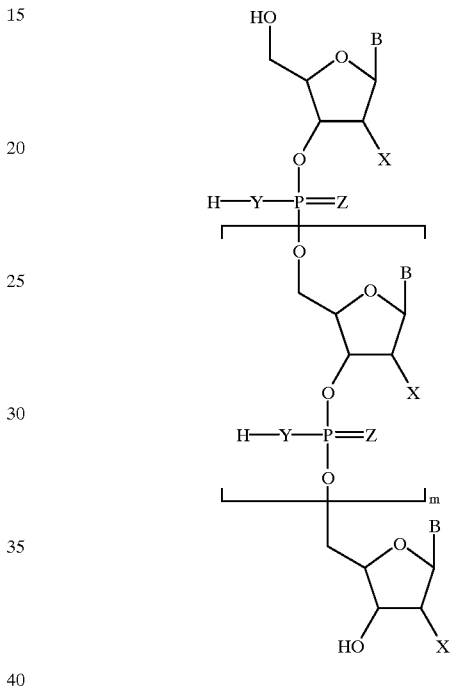

where each B is preferably an unprotecteted heterocyclic base.

Each internucleotide linkage of the sulfurized oligonucleotide analog released from the solid support may be ionized, depending on the pH, temperature and salt conditions. Each internucleotide linkage will be ionized in aqueous solution at physiologic pH, temperature and salt conditions, i.e., pH 7.2, 37° C. and about 150 mM monovalent salts.

Having generally described this invention, a further understanding can be obtained by reference to certain specific examples which are provided herein for purposes of illustration only and are not intended to be limiting unless otherwise specified.

EXAMPLES

Example 1

Diethyldithiocarbonate Disulfide

Potassium ethyl xanthate (120 g) was dissolved in a minimum amount of water. Iodine was added to this solution portionwise at 10° C. until a dark brown color persisted. A small amount of aqueous saturated $Na_2S_2O_3$ was added to quench the reaction and remove the dark brown color from the solution. The resulting solution was extracted with ether. The combined ether layers were washed three times with water, dried and concentrated to afford diethyldithiocarbonate disulfide as a pale yellow solid.

Example 2

Synthesis of a T—T Phosphorothioate Dimer 100 milligrams (4 mmole) of 5'-O-dimethoxytritylthymidine attached to a controlled pore glass (CPG) support by an ester linkage was added to a glass reactor, and solution of 2% dichloroacetic acid in dichloromethane (volume/volume) was added to deprotect the 5'-hydroxyl group. The product was first washed with dichloromethane and then with acetonitrile. A 0.2 M solution of 5'-O-(4,4'-dimethoxytrityl)thymidine-3'-O-(2-cyanoethyl N,N-diisopropylphosphoramidite) in acetonitrile and a 0.4 M solution of 1H-tetrazole in acetonitrile were added, and allowed to react at room temperature for 5 minutes. The product was first washed with acetonitrile, and then a 1 M solution of diethyldithiocarbonate disulfide in pyridine was added and allowed reacted at room temperature for 100 seconds. This sulfurization step was repeated for 100 seconds. The CPG was washed with acetonitrile and then a solution of acetic anhydride/lutidine/THF (1:1:8), and N-methylimidazole/THF was added to cap unreacted 5'-hydroxyl groups. The CPG was then washed with acetonitrile. The CPG was treated with 30% aqueous ammonium hydroxide solution for 90 minutes. The aqueous solution was filtered, concentrated under reduced pressure to afford the desired T-T phosphorothioate dimer.

Example 3

Synthesis of a C-T Phosphorothioate Dimer 100 milligrams (4 mmole) of 5'-O-dimethoxytritylthymidine attached to a CPG support by an ester linkage was added to a glass reactor, and a solution of 2% dichloroacetic acid in dichloromethane (volume/volume) was added to deprotect the 5'-hydroxyl group. The CPG was then washed with acetonitrile. A 0.2 M solution of $N^4$-benzoyl-5'-O-(4,4'-dimethoxytrityl)-2'-deoxycytidine-3'-O-(2-cyanoethyl N,N-diisopropylphosphoramidite) in acetonitrile and a 0.4 M solution of 1H-tetrazole in acetonitrile was added, and allowed to stand at room temperature for 5 minutes. The CPG was then washed with acetonitrile, followed by addition of a 1 M solution of diethyldithiocarbonate disulfide in pyridine. The sulfurization reaction was allowed to procede at room temperature for 100 seconds. The sulfurization step was repeated for an additional 100 seconds. The support was then washed with acetonitrile followed by addition of a solution of acetic anhydride/lutidine/THF (1:1:8), and N-methylimidazole/THF to cap unreacted 5'-hydroxyl groups. After capping, the CPG was washed with acetonitrile. The CPG was treated with 30% aqueous ammonium hydroxide solution for 90 minutes and then incubated at 55° C. for 12 hours. The aqueous solution was filtered, concentrated under reduced pressure to afford the desired C-T phosphorothioate dimer.

Example 4

Synthesis of G-T Phosphorothioate Dimer 100 milligrams (4 mmole) of 5'-O-dimethoxytritylthymidine attatched to a CPG support by an ester linkage was added to a glass reactor, and a 2% solution of dichloroacetic acid in dichloromethane (volume/volume) was added to deprotect the 5'-hydroxyl group. The CPG was washed with dichloromethane and then washed with acetonitrile. A 0.2 M solution of $N^2$-isobutyrl-5'-O-(4,4'-dimethoxytrityl)-2'-deoxyguanosine-3'-O-(2-cyanoethyl N,N-diisopropylphosphoramidite) in acetonitrile and a 0.4 M solution of 1H-tetrazole in acetonitrile was added, and reacted at room temperature for 5 minutes. The product was washed with acetonitrile, and then a 1 M solution of diethyldithiocarbonate disulfide in pyridine was added. The sulurization reaction was allowed to proceed at room temperature for 100 seconds. The sulfurization step was repeated for an additional 100 seconds. The support was washed with acetonitrile and then a solution of acetic anhydride/lutidine/THF (1:1:8), and N-methylimidazole/THF was added to cap any unreacted 5'-hydroxyl groups. The CPG was then washed with acetonitrile. The CPG was treated with 30% aqueous ammonium hydroxide solution for 90 minutes at room temperature and then incubated at 55° C. for 1 hour. The aqueous solution was filtered and concentrated under reduced pressure to give the desired T—T phosphorothioate dimer.

Example 5

Synthesis of a 5'-TTTTTTT-3' Phosphorothioate Heptamer 50 milligrams (2 mmole) of 5'-O-dimethoxytritylthymidine attached to a CPG support by an ester linkage was added to a glass reactor, and a 2% solution of dichloroacetic acid in dichloromethane (volume/volume) was added to deprotect the 5'-hydroxyl group. The CPG was then washed with acetonitrile. A 0.2 M solution of 5'-O-(4,4'-dimethoxytrityl)thymidine-3'-O-(2-cyanoethyl N,N-diisopropylphosphoramidite) in acetonitrile and a 0.4 M solution of 1H-tetrazole in acetonitrile was added, and allowed to react at room temperature for 5 minutes. The CPG was washed with acetonitrile, and then a 1 M solution of diethyldithiocarbonate disulfide in pyridine was added and allowed to react at room temperature for 100 seconds. This sulfurization step was repeated for 100 seconds. The support was washed with acetonitrile, and then a solution of acetic anhydride/lutidine/THF (1:1:8), and N-methylimidazole/THF was added to cap any unreacted 5'-hydroxyl groups. After capping, the solid support was washed with acetonitrile. This complete cycle was repeated five times to afford the protected thymidine heptamer. The support containing the compound was treated with 30% aqueous ammonium hydroxide solution for 90 minutes at room temperature. The aqueous solution is filtered, and concentrated under reduced pressure to afford the desired phosphorothioate heptamer 5'-TTTTTTT-3'.

Example 6

Synthesis of 5'-d(GACTT)-3' Phosphorothioate Pentamer 50 milligrams (2 mmole) of 5'-O-dimethoxytritylthymidine bound to a CPG controlled pore glass support through an ester linkage was added to a glass reactor, and a 2% solution of dichloroacetic acid in dichloromethane (volume/volume) was added to deprotect the 5'-hydroxyl group. The CPG was then washed with acetonitrile. A 0.2 M solution of 5'-O-(4,4'-dimethoxytrityl) thymidine- 3'-O-(2-cyanoethyl N,N-diisopropylphosphoramidite) in acetonitrile and a 0.4 M solution of 1H-tetrazole in acetonitrile were added, and allowed to react at room temperature for 5 minutes. The CPG was washed with acetonitrile, and then a 1 M solution of diethyldithiocarbonate disulfide in pyridine was added and allowed to react at room temperature for 100 seconds. This sulfurization step was repeated for 100 seconds. The support was washed with acetonitrile and then a solution of acetic anhydride/lutidine/THF (1:1:8), and N-methylimidazole/THF was added to cap the unreacted 5'-hydroxyl groups. After capping, the support was washed with acetonitrile.

A solution of 2% dichloroacetic acid in dichloromethane (volume/volume) was added to deprotect the 5'-hydroxyl group, followed by washing with acetonitrile. A 0.2 M solution of $N^4$-benzoyl-5'-O-(4,4'-dimethoxytrityl)-2'-deoxycytidine-3'-O-(2-cyanoethyl N,N-diisopropylphosphoramidite) in acetonitrile and a 0.4 M solution of 1H-tetrazole in acetonitrile were added, and allowed to react at room temperature for 5 minutes. After washing the solid support with acetonitrile, a 1 M solution of diethyldithiocarbonate disulfide in pyridine was added and allowed to react at room temperature for 100 seconds. This sulfurization step was repeated for 100 seconds. The support was washed with acetonitrile and then a solution of acetic anhydride/lutidine/THF (1:1:8), and N-methylimidazole/THF was added to cap any unreacted 5'-hydroxyl groups. The support was washed with acetonitrile.

A solution of 2% dichloroacetic acid in dichloromethane (volume/volume) was added to deprotect the 5'-hydroxyl group. The CPG was washed with acetonitrile. A 0.2 M solution of $N^6$-benzoyl-5'-O-(4,4'-dimethoxytrityl)-2'-deoxyadenosine-3'-O-(2-cyanoethyl N,N-diisopropylphosphoramidite) in anhydrous acetonitrile and a 0.4 M solution of 1H-tetrazole in acetonitrile were added and allowed to react at room temperature for 5 minutes. The product was washed with acetonitrile, and then a 1 M solution of diethyldithiocarbonate disulfide in pyridine was added and allowed to react at room temperature for 5 minutes. This sulfurization step was repeated for 5 minutes. The support was washed with acetonitrile and then a solution of acetic anhydride/lutidine/THF (1:1:8), and N-methylimidazole/THF was added to cap the unreacted 5'-hydroxyl groups. The product is washed with acetonitrile.

A solution of 2% dichloroacetic acid in dichloromethane (volume/volume) was added to deprotect the 5'-hydroxyl group. The product was washed with acetonitrile. Then, a 0.2 M solution of $N^2$-isobutyryl-5'-O-(4,4'-dimethoxytrityl)-2'-deoxyguanosine-3'-O-(2-cyanoethyl N,N-diisopropylphosphoramidite) in acetonitrile and a 0.4 M solution of 1H-tetrazole in acetonitrile were added, and allowed to react at room temperature for 5 minutes. The product was washed with acetonitrile, and then a 1 M solution of diethyldithiocarbonate disulfide in pyridine was added and allowed to react at room temperature for 100 seconds. This sulfurization step was repeated for 100 seconds. The support was washed with acetonitrile and then a solution of acetic anhydride/lutidine/THF (1:1:8), and N-methylimidazole/THF was added to cap any unreacted 5'-hydroxyl groups. The product was washed with acetonitrile.

The CPG was treated with 30% aqueous ammonium hydroxide solution for 90 minutes at room temperature and then incubated at 55° C. for 24 hours. The aqueous solution was filtered, concentrated under reduced pressure to give the desired 5'-d(GACTT)-3' phosphorothioate tetramer.

Example 7

Synthesis of Homo-Thymidine Phosphorothioate 19-mer

A 19-base homo-thymidine phosphorothioate oligonucleotide was synthesized by the phosphoramidite method on an automated synthesizer (ABI model 390Z, Foster City, Calif.). The standard synthesis protocol was followed, except that in place of the oxidation step a sulfurization step was substituted, and this step preceded the capping step. In other words, synthesis consisted of repeated cycles of detritylation, coupling, sulfurization, and capping. Separation of the final product from the synthesis column and purification were accomplished using well-known methods. The sulfurization step involved exposing the growing chain to a 1 M solution of diethyldithiocarbonate disulfide in pyridine for 100 seconds at room temperature.

The yield of trityl cation released during the detritylation steps averaged 99%. The trityl yield is both a measure of coupling efficiency and a measure of the extent of sulfurization, since non-sulfurized trivalent phosphorus linkages in the oligonucleotide are labile to cleavage during detritylation. The 19-mer was cleaved from the support and deprotected with concentrated ammonium hydroxide under standard conditions and isolated using techniques well-known in the art.

Example 8

Large-Scale Synthesis of a 20-mer Phosphorothioate Oligonucleotide Analog

A 20-base phosphorothioate oligonucleotide analog of sequence 5'-TCCCGCCTGTGACATGCATT-3' was synthesized by the phosphormidite method on an OligoPilot automated DNA synthesizer (available from Pharmacia, Sweden). The standard synthesis protocol was used with the oxidation step replaced with a sulfurization step with diethyldithiocarbonate disulfide. Sulfurization of each phosphorous(III) linkage was accomplished by exposing the oligonucleotide analog to a 0.2 M solution of diethyldithiocarbonate disulfide in pyridine/dichloromethane (1:1 v/v) for 100 seconds at room temperature. The resulting 20-mer phosphorothioate oligonucleotide analog was deprotected and cleavage from the solid support with aqueous ammonium hydroxide and purified by well-known methods.

All references cited in the present application are hereby incorporated by reference in their entirety.

Obviously, numerous modifications and variations of the present invention are possible in light of the above teachings. It is therefore to be understood that within the scope of the appended claims, the invention may be practiced otherwise than as specifically described herein.

What is claimed as new and desired to be secured by Letters Patent of the United States is:

1. A method of synthesizing a sulfurized oligonucleotide analog, comprising:

contacting an oligonucleotide analog comprising at least one phosphorous(III) linkage with a solution comprising a solvent and a thiodicarbonic acid diester polysulfide represented by the formula:

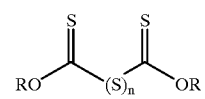

in an automated DNA synthesizer, wherein the solution is in fluid communication with the oligonucleouide analog on the DNA synthesizer, to produce an oligonucleotide analog comprising at least one sulfurized phosphorous(V) linkage, wherein each R is independently selected from the group consisting of $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms and substituted $C_4$–$C_{15}$ heterocycloaralkyl containing up to three heteroatoms; and n is 2, 3 or 4.

2. The method of claim 1, wherein each R is ethyl.

3. The method of claim 1, wherein said phosphorus(III) linkage is a phosphite triester or a thiophosphite triester.

4. The method of claim 1, wherein each R is independently selected from the group consisting of $C_2$–$C_8$ alkyl, substituted $C_2$–$C_8$ alkyl, $C_6$–$C_{14}$ aryl and substituted $C_6$–$C_{14}$ aryl; and n is 2.

5. The method of claim 1, wherein the solvent is selected from the group consisting of acetonitrile, tetrahydrofuran, collidine, dichloromethane, dichloroethane, pyridine, and mixtures thereof.

6. The method of claim 5, wherein the concentration of the thiodicarbonic acid diester polysulfide in the solvent is 0.01 to 1.5 M.

7. The method of claim 5, wherein the concentration of the thiodicarbonic acid diester polysulfide in the solvent is 0.2 to 1.2 M.

8. The method of claim 1, wherein the oligonucleotide analog is attached to a solid support.

9. The method of claim 8, wherein the oligonucleotide analog comprising a phosphorous(III) linkage and attached to a solid support is represented by the formula:

wherein
each Pg is independently a group labile to a base and/or a nucleophile or an allyl group;
$R^6$ is a labile blocking group;
each B is independently an unprotected or protected heterocyclic base;

each X is independently selected from the group consisting of hydrogen, hydroxyl, F, Cl, Br, $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms, substituted $C_4$–$C_{15}$ heterocycloaralkyl containing up to three heteroatoms, O—$C_1$–$C_8$ alkyl, substituted O—$C_1$–$C_8$ alkyl, O—$C_2$–$C_8$ heterocycloalkyl containing up to three heteroatoms, substituted O—$C_2$–$C_8$ heterocycloalkyl containing up to three heteroatoms, O—$C_6$–$C_{14}$ aryl, substituted O—$C_6$–$C_{14}$ aryl, O—$C_3$–$C_{11}$ hetaryl containing up to three heteroatoms, substituted O—$C_3$–$C_{11}$ hetaryl containing up to three heteroatoms, O—$C_7$–$C_{18}$ aralkyl, substituted O—$C_7$–$C_{18}$ aralkyl, O—$C_4$–$C_{15}$ heterocycloaralkyl containing up to three heteroatoms, substituted O—$C_4$–$C_{15}$ heterocycloaralkyl containing up to three heteroatoms, O—$C_1$–$C_8$-alkyl-O—$C_1$–$C_8$-alkyl, O—$C_1$–$C_8$ alkenyl, O—$C_1$–$C_8$ alkoxyamino, O-tri-$C_1$–$C_8$-alkyl silyl, substituted O-tri-$C_1$–$C_8$-alkyl silyl, NH—$C_1$–$C_8$ alkyl, N—$(C_1$–$C_8)_2$, NH—$C_1$–$C_8$ alkenyl, N—$(C_1$–$C_8)_2$ alkenyl, S—$C_1$–$C_8$ alkyl, S—$C_1$–$C_8$ alkenyl, $NH_2$, $N_3$, NH—$C_1$–$C_8$-alkyl-$NH_2$, polyalkylamino and an RNA cleaving group;

each Y is independently O or S;
each Z is independently O or S;
L is a group labile to a nucleophile and/or base;
$S^p$ is a solid support; and
m is 0 or a positive integer.

10. The method of claim 9, wherein
each R is independently selected from the group consisting of $C_2$–$C_8$ alkyl, substituted $C_2$–$C_8$ alkyl, $C_6$–$C_{14}$ aryl and substituted $C_6$–$C_{14}$ aryl;
n is 2; and
m is an integer between 0 and 198.

11. The method of claim 9, wherein X is hydrogen.

12. The method of claim 9, wherein
each Pg is independently selected from the group consisting of β-cyanoethyl, 4-cyano-2-butenyl, 2-diphenylmethylsilyl and a 2-N-amidoethyl group having the formula $R^1CONR^2CHR^3CHR^4$—;

each $R^1$ is independently selected from the group consisting of $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms and substituted $C_4$–$C_{15}$ heterocycloaralkyl containing up to three heteroatoms;

each $R^2$, $R^3$ and $R^4$ is independently selected from the group consisting of hydrogen, $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7-C_{18}$ aralkyl, $C_4-C_{15}$ heterocycloaralkyl containing up to three heteroatoms and substituted $C_4-C_{15}$ heterocycloaralkyl containing up to three heteroatoms, or $R^3$ and $R^4$ together with the carbon atoms they are bonded to form a $C_3-C_8$ cycloalkyl group, a substituted $C_3-C_8$ cycloalkyl group, a $C_2-C_8$ heterocycloalkyl group containing up to three heteroatoms or a substituted $C_2-C_8$ heterocycloalkyl group containing up to three heteroatoms;

$R^6$ is selected from the group consisting of 4,4'-dimethoxytrityl, monomethoxytrityl, diphenylmethyl, phenylxanthen-9-yl and 9-(p-methoxyphenyl)xanthen-9-yl; and each B is independently selected from the group consisting of adenine, guanine, cytosine, thymine, uracil, 2-aminopurine, inosine and 5-methylcytosine, where the exocyclic amino group of each base is protected with an acyl group.

13. A composition for synthesizing sulfurized oligonucleotide analogs, comprising:

a thiodicarbonic acid diester polysulfide represented by the formula:

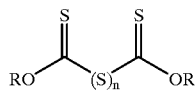

in contact with a solid support suitable for synthesizing oligonucleotide analogs to which is attached thereto an oligonucleotide analog comprising a phosphorous(III) linkage represented by the formula:

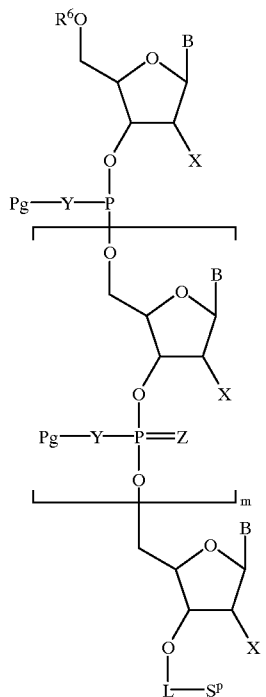

wherein each R is independently selected from the group consisting of $C_1-C_8$ alkyl, substituted $C_1-C_8$ alkyl, $C_2-C_8$ heterocycloalkyl containing up to three heteroatoms, substituted $C_2-C_8$ heterocycloalkyl containing up to three heteroatoms, $C_6-C_{14}$ aryl, substituted $C_6-C_{14}$ aryl, $C_3-C_{11}$ hetaryl containing up to three heteroatoms, substituted $C_3-C_{11}$ hetaryl containing up to three heteroatoms, $C_7-C_{18}$ aralkyl, substituted $C_7-C_{18}$ aralkyl, $C_4-C_{15}$ heterocycloaralkyl containing up to three hetero atoms and substituted $C_4-C_{15}$ heterocycloaralkyl containing up to three heteroatoms;

n is 2, 3 or 4 each Pg is independently a group labile to a base and/or a nucleophile or an allyl group;

$R^6$ is a labile blocking group;

each B is independently an unprotected or protected heterocyclic base;

each X is independently selected from the group consisting of hydrogen, hydroxyl, F, Cl, Br, $C_1-C_8$ alkyl, substituted $C_1-C_8$ alkyl, $C_2-C_8$ heterocycloalkyl containing up to three heteroatoms, substituted $C_2-C_8$ heterocycloalkyl containing up to three heteroatoms, $C_6-C_{14}$ aryl, substituted $C_6-C_{14}$ aryl, $C_3-C_{11}$ hetaryl containing up to three heteroatoms, substituted $C_3-C_{11}$ hetaryl containing up to three heteroatoms, $C_7-C_{18}$ aralkyl, substituted $C_7-C_{18}$ aralkyl, $C_4-C_{15}$ heterocycloaralkyl containing up to three heteroatoms, substituted $C_4-C_{15}$ heterocycloaralkyl containing up to three heteroatoms, O—$C_1-C_8$ alkyl, substituted O—$C_1-C_8$ alkyl, O—$C_2-C_8$ heterocycloalkyl containing up to three heteroatoms, substituted O—$C_2-C_8$ heterocycloalkyl containing up to three heteroatoms, O—$C_6-C_{14}$ aryl, substituted O—$C_6-C_{14}$ aryl, O—$C_3-C_{11}$ hetaryl containing up to three heteroatoms, substituted O—$C_3-C_{11}$ hetaryl containing up to three heteroatoms, O—$C_7-C_{18}$ aralkyl, substituted O—$C_7-C_{18}$ aralkyl, O—$C_4-C_{15}$ heterocycloaralkyl containing up to three heteroatoms, substituted O—$C_4-C_{15}$ heterocycloaralkyl containing up to three heteroatoms, O—$C_1-C_8$-alkyl-O—$C_1-C_8$-alkyl, O—$C_1-C_8$ alkenyl, O—$C_1-C_8$ alkoxyamino, O-tri-$C_1-C_8$-alkyl silyl, substituted O-tri-$C_1-C_8$-alkyl silyl, NH—$C_1-C_8$ alkyl, N—$(C_1-C_8)_2$, NH—$C_1-C_8$ alkenyl, N—$(C_1-C_8)_2$ alkenyl, S—$C_1-C_8$ alkyl, S—$C_1-C_8$ alkenyl, $NH_2$, $N_3$, NH—$C_1-C_8$-alkyl-$NH_2$, polyalkylamino and an RNA cleaving group;

each Y is independently O or S;

each Z is independently O or S;

L is a group labile to a nucleophile and/or base;

$S^p$ is a solid support; and m is 0 or a positive integer.

14. The composition of claim 13, wherein each R is independently selected from the group consisting of $C_2-C_8$ alkyl, substituted $C_2-C_8$ alkyl, $C_6-C_{14}$ aryl and substituted $C_6-C_{14}$ aryl; and n is 2.

15. The composition of claim 13, wherein the solid support is controlled pore glass, a polystyrene resin or a polystyrene/divinylbenzene copolymer resin.

16. The composition of claim 13, wherein each R is independently selected from the group consisting of $C_2-C_8$ alkyl, substituted $C_2-C_8$ alkyl, $C_6-C_{14}$ aryl and substituted $C_6-C_{14}$ aryl;

n is 2; and m is an integer between 0 and 198.

17. The composition of claim 13, wherein X is hydrogen.

18. The composition of claim 13, wherein each Pg is independently selected from the group consisting of β-cyanoethyl, 4-cyano-2-butenyl, 2-diphenylmethylsilyl and a 2-N-amidoethyl group having the formula $R^1CONR^2CHR^3CHR^4$—;

each $R^1$ is independently selected from the group consisting of $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms and substituted $C_4$–$C_{15}$ heterocycloaralkyl containing up to three heteroatoms, each $R^2$, $R^3$ and $R^4$ is independently selected from the group consisting of hydrogen, $C_1$–$C_8$ alkyl, substituted $C_1$–$C_8$ alkyl, $C_2$–$C_8$ heterocycloalkyl containing up to three heteroatoms, substituted $C_2$–$C_8$ heterocycloalkyl containing up to three heteroatoms, $C_6$–$C_{14}$ aryl, substituted $C_6$–$C_{14}$ aryl, $C_3$–$C_{11}$ hetaryl containing up to three heteroatoms, substituted $C_3$–$C_{11}$ hetaryl containing up to three heteroatoms, $C_7$–$C_{18}$ aralkyl, substituted $C_7$–$C_{18}$ aralkyl, $C_4$–$C_{15}$ heterocycloaralkyl containing up to three heteroatoms and substituted $C_4$–$C_{15}$ heterocycloaralkyl containing up to three heteroatoms, or $R^3$ and $R^4$ together with the carbon atoms they are bonded to form a $C_3$–$C_8$ cycloalkyl group, a substituted $C_3$–$C_8$ cycloalkyl group, a $C_2$–$C_8$ heterocycloalkyl group containing up to three heteroatoms or a substituted $C_2$–$C_8$ heterocycloalkyl group containing up to three heteroatoms;

$R^6$ is selected from the group consisting of 4,4'-dimethoxytrityl, monomethoxytrityl, diphenylmethyl, phenylxanthen-9-yl and 9-(p-methoxyphenyl)xanthen-9-yl; and each B is independently selected from the group consisting of adenine, guanine, cytosine, thymine, uracil, 2-aminopurine, inosine and 5-methylcytosine, where the exocyclic amino group of each base is protected with an acyl group.

* * * * *